US 9,107,643 B2

United States Patent
Chang

(10) Patent No.: US 9,107,643 B2
(45) Date of Patent: Aug. 18, 2015

(54) X-RAY DETECTOR, X-RAY DETECTION SYSTEM HAVING THE SAME, AND X-RAY DETECTION METHOD

(71) Applicant: Sung ho Chang, Yongin (KR)

(72) Inventor: Sung ho Chang, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 100 days.

(21) Appl. No.: 13/944,074

(22) Filed: Jul. 17, 2013

(65) Prior Publication Data

US 2014/0072107 A1    Mar. 13, 2014

(30) Foreign Application Priority Data

Sep. 11, 2012 (KR) ........................ 10-2012-0100579

(51) Int. Cl.
*A61B 6/00* (2006.01)

(52) U.S. Cl.
CPC .............. *A61B 6/587* (2013.01); *A61B 6/588* (2013.01); *A61B 6/4233* (2013.01)

(58) Field of Classification Search
CPC .......... A61B 6/587; A61B 6/588; A61B 6/08; A61B 6/547; A61B 6/4233; A61B 6/4405
USPC ................. 378/162, 163, 164, 204, 205, 210; 342/463
See application file for complete search history.

(56) References Cited

U.S. PATENT DOCUMENTS

| | | | | |
|---|---|---|---|---|
| 6,092,928 | A | * | 7/2000 | Mattson et al. ............... 378/205 |
| 2007/0001905 | A1 | | 1/2007 | Eronen |
| 2007/0041508 | A1 | * | 2/2007 | Tubbs ........................... 378/207 |
| 2008/0240357 | A1 | * | 10/2008 | Jabri et al. .................... 378/101 |
| 2009/0257564 | A1 | * | 10/2009 | Kito et al. ..................... 378/206 |
| 2010/0080349 | A1 | * | 4/2010 | Kalender et al. ................ 378/37 |
| 2010/0096558 | A1 | * | 4/2010 | Danielsson et al. ..... 250/370.11 |

FOREIGN PATENT DOCUMENTS

| | | |
|---|---|---|
| KR | 10-2010-0013348 A | 2/2010 |
| KR | 10-2010-0109381 A | 10/2010 |
| KR | 10-2012-0009812 A | 2/2012 |

OTHER PUBLICATIONS

Priyantha et. al., Anchor Free Distributed Localization in Sensor Networks, Apr. 2003, Tech Report #892, MIT Laboratory for Computer Science, p. 1.*

* cited by examiner

*Primary Examiner* — Glen Kao
*Assistant Examiner* — Julio M Duarte-Carvajali
(74) *Attorney, Agent, or Firm* — Lee & Morse, P.C.

(57) ABSTRACT

An X-ray detection system includes an X-ray generation device and an X-ray detector. The X-ray generation device includes an X-ray emission unit and a first sensor unit. The X-ray detector includes an X-ray reception unit for receiving X-rays from the X-ray emission unit, a data detection unit for detecting data from the X-ray reception unit, a second sensor unit, a computation unit for computing correction data using a distance between the first sensor unit and the second sensor unit, and a data correction unit for receiving a data signal from the data detection unit, receiving the correction data from the computation unit, and then generating corrected data.

17 Claims, 6 Drawing Sheets

US 9,107,643 B2

X-RAY DETECTOR, X-RAY DETECTION SYSTEM HAVING THE SAME, AND X-RAY DETECTION METHOD

The present application claims priority under U.S.C §119 to Korean Patent Application No. 10-2012-0100579 filed on Sep. 11, 2012, in the Korean Intellectual Property Office, and entitled: "X-Ray Detector X-Ray Detection System Having the Same and X-Ray Detection Method," which is incorporated herein by reference herein its entirety.

BACKGROUND OF THE INVENTION

1. Field of the Invention

Embodiments relate to an X-ray detector, an X-ray detection system having the X-ray detector, and an X-ray detection method.

2. Description of the Related Art

An X-ray detection system refers to a system for emitting X-rays to an object, such as a human body, detecting the amount of X-rays transmitted through the object, and capturing an internal organization of the object. An X-ray imaging system has been generally used as medical examination equipment, non-destructive inspection equipment, etc.

An initial X-ray detection system has captured images using film or Computed Radiography (CR). However, for the reason of convenient use or the like, images have recently been captured using Digital Radiography (DR).

SUMMARY OF THE INVENTION

One or more embodiments are directed to an X-ray detection system including an X-ray generation device including an X-ray emission unit and a first sensor unit, and an X-ray detector including an X-ray reception unit for receiving X-rays from the X-ray emission unit, a data detection unit for detecting data from the X-ray reception unit, a second sensor unit, a computation unit for computing correction data using a distance between the first sensor unit and the second sensor unit, and a data correction unit for receiving a data signal from the data detection unit, receiving the correction data from the computation unit, and then generating corrected data.

One or more embodiments are directed to an X-ray detection system including an X-ray generation device including an X-ray emission unit and a first wireless transceiver, and an X-ray detector including an X-ray reception unit for receiving X-rays from the X-ray emission unit, and a second wireless transceiver, a third wireless transceiver, and a fourth wireless transceiver arranged around the X-ray reception unit.

One or more embodiments are directed to an X-ray detector including an X-ray reception unit including a plurality of pixels for converting received X-rays into current signals, and a plurality of wireless transceivers arranged around the X-ray reception unit.

One or more embodiments are directed to an X-ray detection method including defining a first corner, a second corner, a third corner, and a fourth corner of a first quadrangle in an X-ray detector, obtaining a first straight line for connecting an X-ray generation device and the first corner, a second straight line for connecting the X-ray generation device and the second corner, a third straight line for connecting the X-ray generation device and the third corner, and a fourth straight line for connecting the X-ray generation device and the fourth corner, calculating an area of a second quadrangle defined by points present on the respective straight lines, the points being individually located at an identical distance from the X-ray generation device, calculating a ratio of areas by dividing the area of the second quadrangle by an area of the first quadrangle, and correcting an amount of X-rays incident on the X-ray detector from the X-ray generation device using the ratio of areas.

BRIEF DESCRIPTION OF THE DRAWINGS

The above and other aspects and features will become more apparent by describing in detail exemplary embodiments thereof with reference to the attached drawings, in which.

DESCRIPTION OF THE PREFERRED EMBODIMENTS

Figure 1:
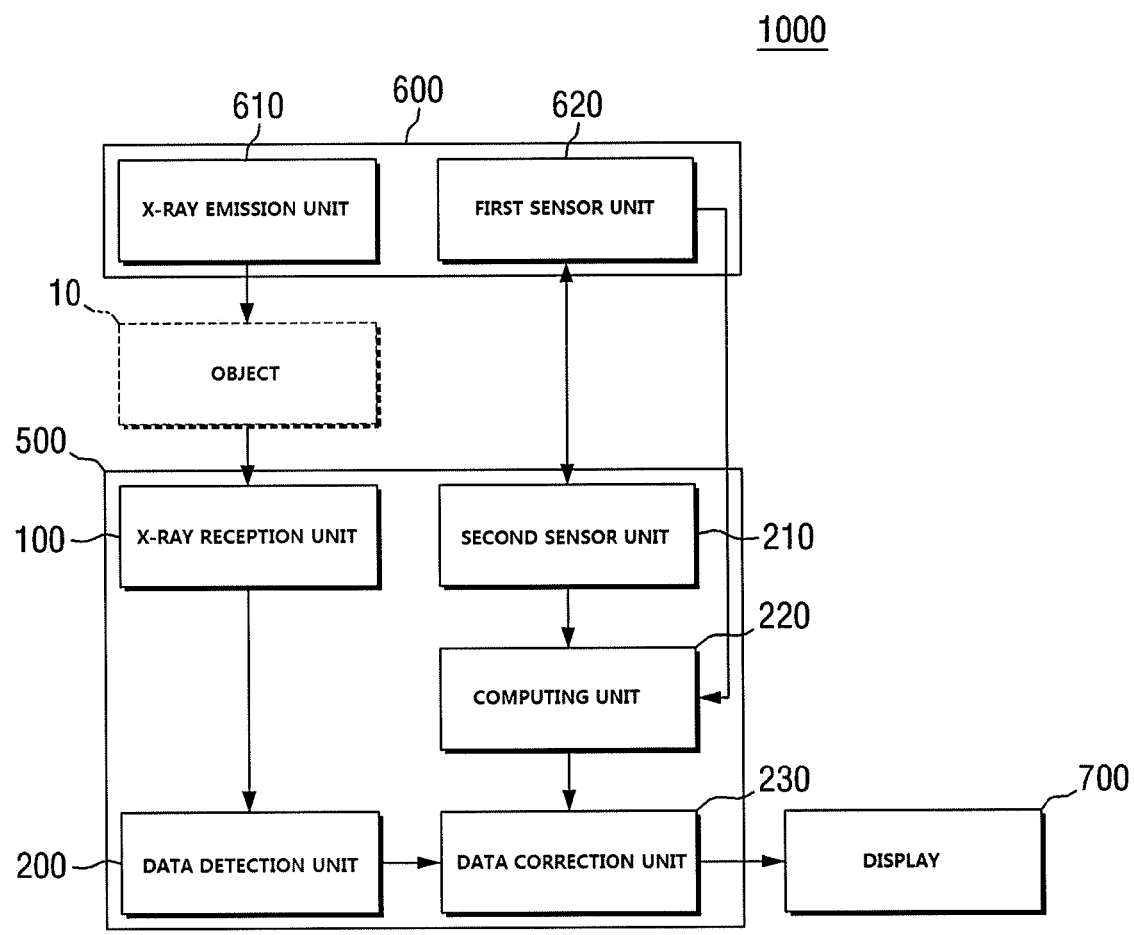
FIG. 1 is a block diagram showing an X-ray detection system according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. Like reference numerals refer to like elements throughout.

In the description, an expression indicating that a first element or layer is disposed "on" a second element or layer includes the cases where the first element or layer is directly disposed on the second element or layer and where a certain element or layer is interposed between the first and second elements or layers. Throughout the entire specification, the same reference numerals are used to designate the same or similar components.

Although the terms "first", "second", etc. are used to describe various components, it is apparent that the components are not limited by those terms. These terms are merely used to distinguish one component from other components. Therefore, it is apparent that a first component described below may be a second component within the technical spirit of the present disclosure.

Hereinafter, embodiments will be described with reference to the attached drawings.

FIG. 1 is a block diagram showing an X-ray detection system according to an embodiment. Referring to FIG. 1, an X-ray detection system 1000 includes an X-ray generation device 600, an X-ray detector 500, and a display 700.

The X-ray generation device 600 includes an X-ray emission unit 610 and a first sensor unit 620.

The X-ray emission unit 610 may generate and emit X-rays and cause the X-rays to be incident on an object 10.

The first sensor unit 620 can compute various types of information, such as a relationship between relative locations of the X-ray generation device 600 and the X-ray detector 500, which will be described later, and a distance and an angle between the X-ray generation device 600 and the X-ray detector 500, by communicating with the second sensor unit 210 of the X-ray detector 500. A description of this function will be given in detail later.

The X-ray detector 500 includes an X-ray reception unit 100, a data detection unit 200, the second sensor unit 210, a computation unit 220, and a data correction unit 230. First, the X-ray reception unit 100 and the data detection unit 200 are described below.

The X-ray reception unit 100 converts X-rays having passed through the object 10 into electrical signals. The data detection unit 200 detects data about the electrical signals converted by the X-ray reception unit 100, and analyzes the data. For a detailed description thereof will be provided by referring to FIG. 2.

Figure 2:
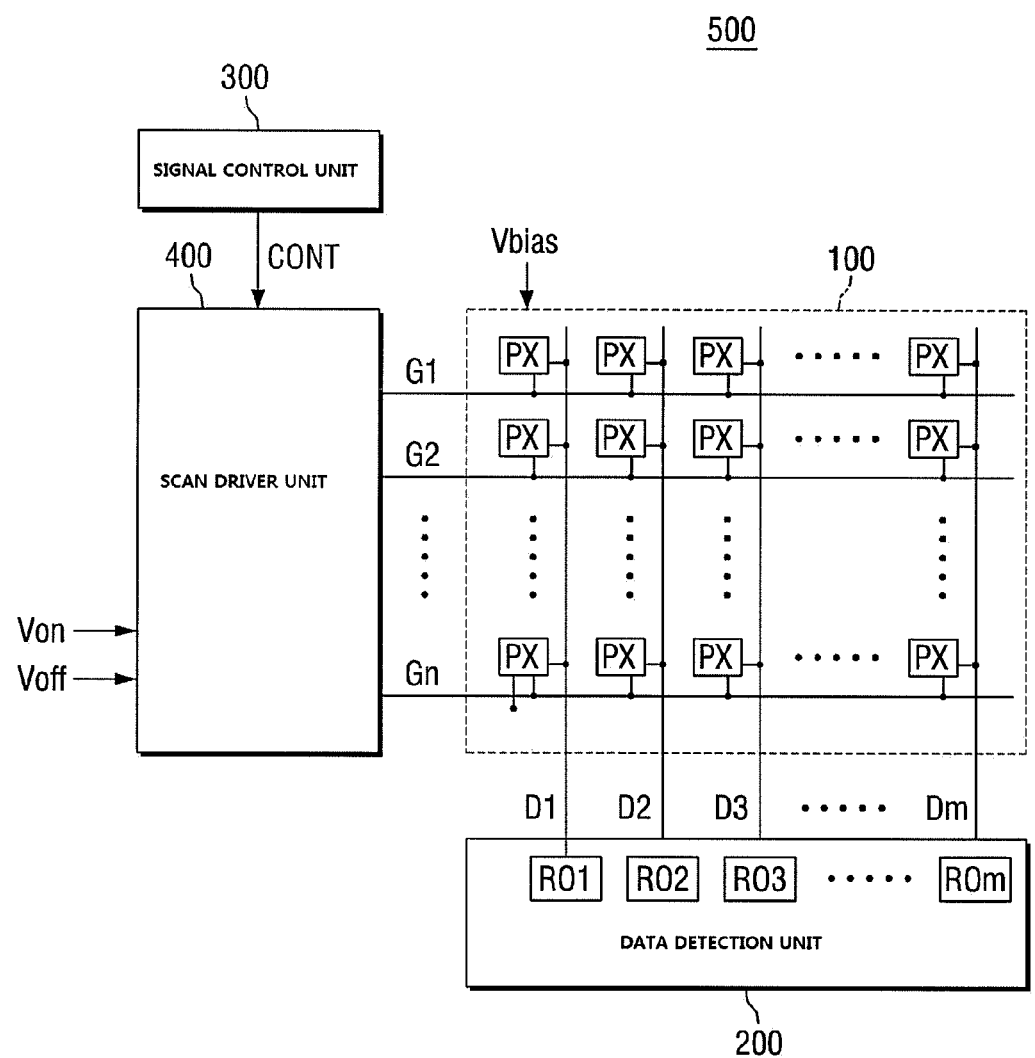
FIG. 2 is a schematic diagram showing the X-ray detector of the X-ray detection system according to an embodiment.

FIG. 2 is a schematic diagram showing the X-ray detector 500 of the X-ray detection system according to an embodiment. As shown in FIG. 2, the X-ray reception unit 100 may include a plurality of scan lines G1 to Gn, a plurality of data lines D1 to Dm, and a plurality of light-sensing pixels PX. The plurality of light-sensing pixels PX may be connected to the plurality of signal lines G1 to Gn and D1 to Dm, and may be arranged in a matrix form. The scan lines S1 to Sn may extend along the direction of rows and be almost parallel with one another. The data lines D1 to Dm may extend along the direction of columns and be substantially parallel with one another. A bias voltage Vbias for operating each of the light-sensing pixels PX may be supplied to the X-ray reception unit 100.

When the X-ray detector 500 is an indirect type, a scintillator layer (not shown) for converting X-rays into visible rays may be disposed on the surface of the X-ray reception unit 100 on which the X-rays are incident. The scintillator layer may be made of cesium iodine (CsI), gadolinium oxysulfide (GOS), or the like.

When the X-ray detector 500 is a direct type, the X-ray reception unit 100 may include a photoconductive layer (not shown). The photoconductive layer may include at least one of amorphous Si (a-Si), $HgI_2$, $PbI_2$, CdTe, and CdZnTe.

The X-ray detector 500 may further include a signal control unit 300 and a scan driver unit 400.

The signal control unit 300 generates a scan driving signal CONT in response to a signal supplied from an external device. The scan driving signal CONT is used to control the operation of the scan driver unit 400. The signal control unit 300 provides the generated scan driving signal CONT to the scan driver unit 400.

The scan driver unit 400 is connected to the scan lines G1 to Gn of the X-ray reception unit 100, and is configured to generate a plurality of scan signals implemented as combinations of a gate-on voltage Von for turning on a switching transistor and a gate-off voltage Voff for turning off the switching transistor in response to the scan driving signal CONT, and apply the scan signals to the plurality of scan lines G1 to Gn, respectively. The scan signals are used to control the output of data signals from the X-ray reception unit 100.

The data detection unit 200 includes readout units RO1 to ROm respectively connected to the data lines D1 to Dm of the X-ray reception unit 100. The respective readout units RO1 to ROm may receive and read currents transferred from the light-sensing pixels PX of the X-ray reception unit 100 through the respective data lines D1 to Dm, and then generate digital data signals.

Referring back to FIG. 1, the second sensor unit 210 may compute information, such as a relationship between relative locations of the X-ray generation device 600 and the X-ray detector 500, and a distance and an angle between the X-ray generation device 600 and the X-ray detector 500, by communicating with the first sensor unit 620.

Figure 3:
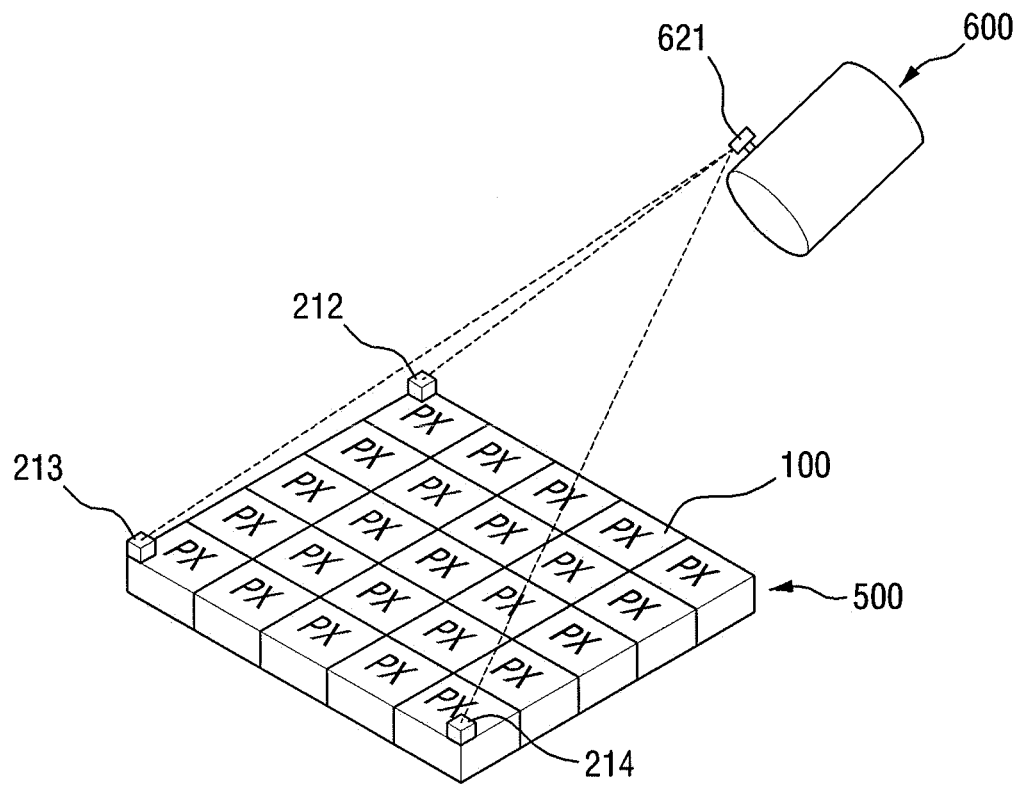
FIG. 3 is a schematic perspective view showing the X-ray detection system according to an embodiment.

FIG. 3 is a schematic perspective view showing the X-ray detection system according to an embodiment. Referring to FIG. 3, the first sensor unit 620 of the X-ray generation device 600 may include at least one sensor, and the second sensor unit 210 of the X-ray detector 500 may include at least three sensors. The individual sensors may measure mutual distances and/or angles.

In an exemplary embodiment, the sensor of the first sensor unit 620 may be a first wireless transceiver 621. The three sensors installed in the second sensor unit 210 may be second to fourth wireless transceivers 212, 213, and 214.

The first to fourth wireless transceivers 621, 212, 213, and 214 may be Radio Frequency (RF) transceivers or Wireless Fidelity (WiFi) transceivers. When the WiFi transceivers are used, the frequency used may be, but not limited to, 2.4 GHz, 5 GHZ, or the like.

The locations at which the second to fourth wireless transceivers 212, 213, and 214 are arranged may be determined by defining a single plane. That is, when each of the locations at which the respective wireless transceivers are arranged is caused to correspond to a single point, only a single plane passing through the three points can be defined. When the three wireless transceivers 212, 213, and 214 are arranged on one surface of the X-ray detector 500 forming the single plane, the location and angle of the X-ray detector 500 can be more easily calculated.

The locations of the second to fourth wireless transceivers 212, 213, and 214 in the X-ray detector 500 may be arranged around the X-ray reception unit 100, but may be freely positioned. When the X-ray detector 500 has the shape of a rectangle, the wireless transceivers may be arranged adjacent to three of a total of four corners so as to efficiently calculate a more precise distance and location. In an exemplary embodiment, the X-ray detector 500 may have the shape of a first quadrangle R1 including first, second, third, and fourth corners, and the second wireless transceiver 212, the third wireless transceiver 213, and the fourth wireless transceiver 214 may be arranged at the second corner, the third corner, and the fourth corner, respectively.

The respective wireless transceivers 621, 212, 213, and 214 can calculate mutual distances by communicating with one another. Since the second to fourth wireless transceivers 212, 213, and 214 are fixed in the X-ray detector 500, distances and angles between them are also fixed. Accordingly, when the calculation of the distances between the second to fourth wireless transceivers 212, 213, and 214 is unnecessary, separate communication among the wireless transceivers 212, 213, and 214 may not be performed.

Meanwhile, the first wireless transceiver 621 is installed on the X-ray generation device 600, and the X-ray generation device 600 is arranged independently of the X-ray detector 500. In particular, in the case of an X-ray detection system 1000 having a movable X-ray detector 500, the X-ray generation device 600 is configured such that a relative distance and a relative angle between the X-ray generation device 600 and the X-ray detector 500 are not fixed, but are fluid. Therefore, in order to measure the relative displacement between the X-ray generation device 600 and the X-ray detector 500, the second to fourth wireless transceivers 212, 213, and 214 may communicate with the first wireless transceiver 621. In an exemplary embodiment, the second, third, and fourth wireless transceiver 212, 213, and 214 may sequentially transmit respective wireless signals, and the first wireless transceiver 621 may receive the wireless signals and calculate distances between the respective wireless transceivers. In contrast, the first wireless transceiver 621 may transmit a wireless signal, and the second to fourth wireless transceivers 212, 213, and 214 may receive the wireless signal and calculate distances between the wireless transceivers.

In another exemplary embodiment, the first wireless transceiver 621 may transmit a wireless signal, and compare the times at which the second to fourth wireless transceivers 212, 213, and 214 receive the wireless signal, so that distances between the wireless transceivers can be calculated. For this, a time synchronization signal may be previously input to the first to fourth wireless transceivers 621, 212, 213, and 214, so that respective times can be synchronized among the wireless transceivers 621, 212, 213, and 214.

In the embodiment of FIG. 3, the case where all of the sensor of the first sensor unit 620 and the sensors of the second sensor unit 210 are wireless transceivers is exemplified, but the sensors may be wired transceivers. Further, the sensors may take charge of either transmission or reception in such a way that the sensor of the first sensor unit 620 is a wired/wireless receiver and the sensors of the second sensor unit 210 are wired/wireless transmitters. In a further exemplary embodiment, the sensor of the first sensor unit 620 or the sensors of the second sensor unit 210 may be radar transceivers.

Referring back to FIG. 1, the distances measured between the first wireless transceiver 621 and the second to fourth wireless transceivers 212, 213, and 214 are input to the computation unit 220.

The computation unit 220 computes correction data using the input distances. The computed correction data is transferred to the data correction unit 230. A detailed description of the correction data is described below with reference to FIGS. 4 and 5.

Figure 4:
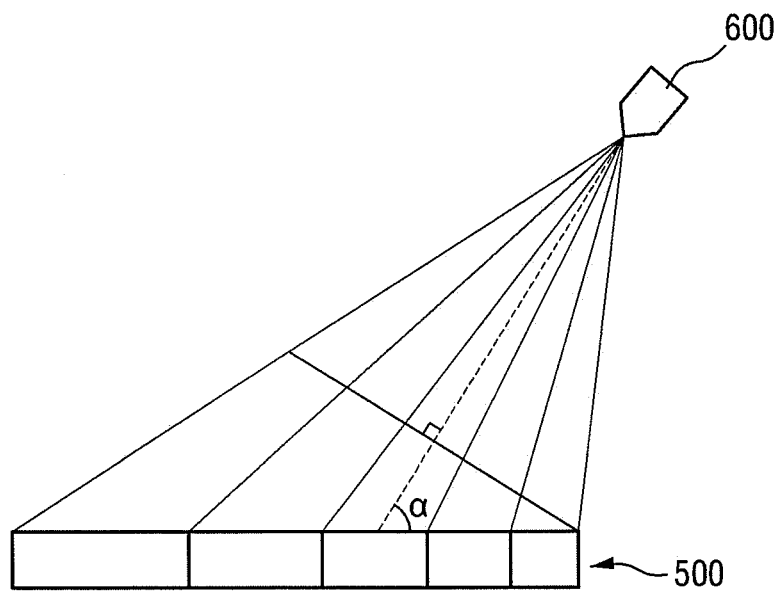
FIG. 4 is a schematic diagram showing the X-ray detection system according to an embodiment.

FIG. 4 is a schematic diagram showing the X-ray detection system according to an embodiment. Referring to FIG. 4, the amount of X-rays is inversely proportion to the square of the traveling distance of the X-rays. Accordingly, when the center line of the X-rays has an angle of inclination α, such as an acute angle or an obtuse angle, with respect to the X-ray detector 500, without being perpendicular to the X-ray detector 500, an image acquired by the X-ray detector 500 cannot represent the amount of X-rays that were actually emitted, without change. Therefore, the quality of image data and the acquired image may be degraded.

The amount of X-rays that have reached the pixels of the X-ray detector 500 in the X-ray detection system 1000 may be a criterion for determining whether a specific material is present. In this way, when the amount of X-rays detected is false, there is the risk of erroneously recognizing the specific material as another material, or falsely determining that the specific material is not present even if the specific material is actually present. The above-described correction data is used to prevent such degradation of image quality.

Figure 5:
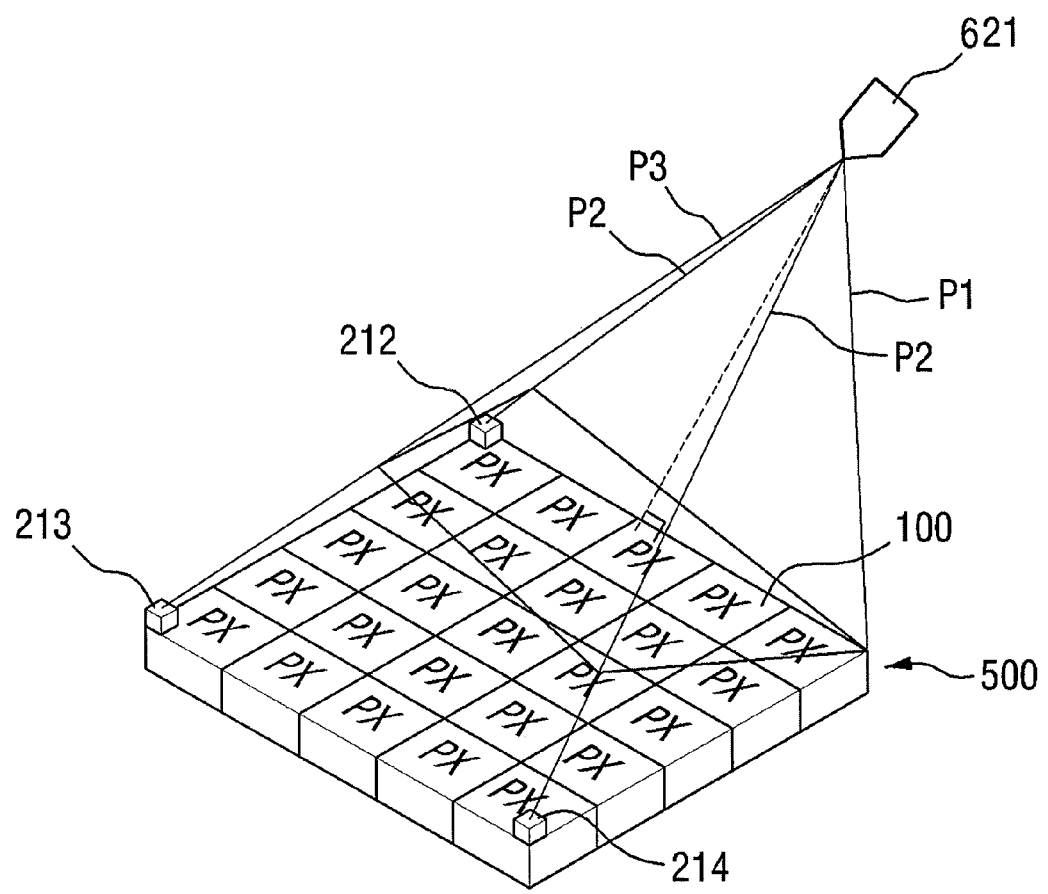
FIG. 5 is a perspective view showing a method of computing correction data in the X-ray detection system according to an embodiment.

FIG. 5 is a perspective view showing a method of calculating correction data in the X-ray detection system according to an embodiment. Referring to FIG. 5, when a distance d2 between the first wireless transceiver 621 and the second wireless transceiver 212, a distance d3 between the first wireless transceiver 621 and the third wireless transceiver 213, and a distance d4 between the first wireless transceiver 621 and the fourth wireless transceiver 214 are determined, the relative displacements of the second to fourth wireless transceivers 212, 213, and 214 to the first wireless transceiver 621 can be determined because a figure defined by the second to fourth wireless transceivers 212, 213, and 214 has already been determined on the X-ray detector 500. Furthermore, since the first corner forms one corner of a rectangle as it is disposed on the plane defined by the second to fourth wireless transceivers 212, 213, and 214, the relative displacement thereof can be calculated together with the above relative displacements.

Therefore, a first straight line P1 for connecting the first wireless transceiver 621 and the first corner, a second straight line P2 for connecting the first wireless transceiver 621 and the second wireless transceiver 212, a third straight line P3 for connecting the first wireless transceiver 621 and the third wireless transceiver 213, and a fourth straight line P4 for connecting the first wireless transceiver 621 and the fourth wireless transceiver 214 in a three-dimensional (3D) coordinate system may be calculated.

If points located at the same distance to the first wireless transceiver 621 are taken from the respective straight lines P1, P2, P3, and P4, a second quadrangle R2 can be defined. In an exemplary embodiment, the points taken at the same distance may be, but not limited to, points closest to the first wireless transceiver 621 from the first corner and the second to fourth wireless transceivers 212 to 214.

An area S2 of the second quadrangle R2 is calculated, and a ratio of areas S2/S1 obtained by dividing the area S2 of the second quadrangle by an area S1 of the first quadrangle R1 that is an area of the X-ray detector 500 may correspond to the ratio of the amount of incident X-rays to the total amount of X-rays. The ratio of areas S2/S1 is calculated as correction data.

Referring back to FIG. 1, the digital data signals generated by the data detection unit 200 and the correction data, that is, the ratio of areas S2/S1, are input to the data correction unit 230. The data correction unit 230 performs computation on the digital data signals and the ratio of areas S2/S1, and then generates corrected digital data signals. The computation on the area ratio S2/S1 and the digital data signals may be an operation of dividing the digital data signals by the area ratio, but is not limited thereto.

In some embodiments, the data correction unit 230 may further receive first reference image data $I_D$ calculated as a mean value of a plurality of images obtained without emitting X-rays, and second reference image data $I_B$ calculated as a mean value of a plurality of images obtained by emitting X-rays without using an object. The first reference image data $I_D$ and the second reference image data $I_B$ may be stored in memory. The first reference image data $I_D$ and the second reference image data $I_B$ may be calculated together with the area ratio S2/S1 that is the correction data, and may be used to generate corrected data signals.

The corrected digital data signals may be transferred to the display 700, so that an image based on the detection of the X-rays is output.

As described above, in the X-ray detection system according to the present embodiment, the X-ray detector corrects the amount of X-rays incident on the pixels using distance data obtained from the first wireless transceiver 621 and the second to fourth wireless transceivers 212, 213, and 214, thus preventing the degradation of image quality.

Figure 6:
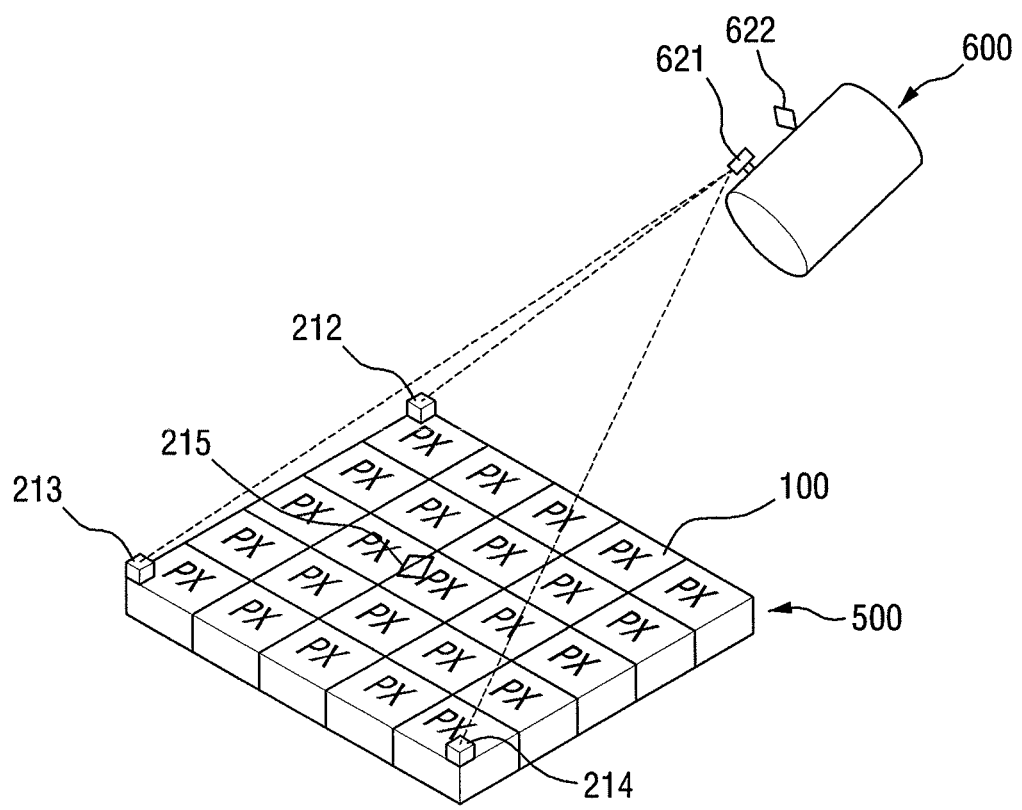
FIG. 6 is a schematic perspective view showing an X-ray detection system according to another embodiment.

FIG. 6 is a schematic perspective view showing an X-ray detection system according to another embodiment. Referring to FIG. 6, the X-ray detection system according to the present embodiment is different from the embodiment of FIG. 3 in that the first sensor unit 620 of an X-ray generation device 600 further includes a first gyro sensor 622, and the second sensor unit 210 of an X-ray detector 500 further includes a second gyro sensor 215.

An angle between the X-ray generation device 600 and the X-ray detector 500 can be calculated by the first gyro sensor 622 and the second gyro sensor 215. A relationship between relative locations of the X-ray generation device 600 and the X-ray detector 500 can be more exactly calculated using the angle calculated in this way.

The arrangement of the first gyro sensor 622 and the second gyro sensor 215 at the center portion of the corresponding device may be expedient for the calculation of an exact angle. However, the locations of the gyro sensors 622 and 215 can be estimated as long as they are already known, so that various locations other than the center portion can also be selected. In some embodiments, the first gyro sensor 622 can be arranged on the center line of X-rays that are emitted. In some embodiments, the second gyro sensor 215 may be arranged at the center portion of the X-ray reception unit 100.

Figure 7:
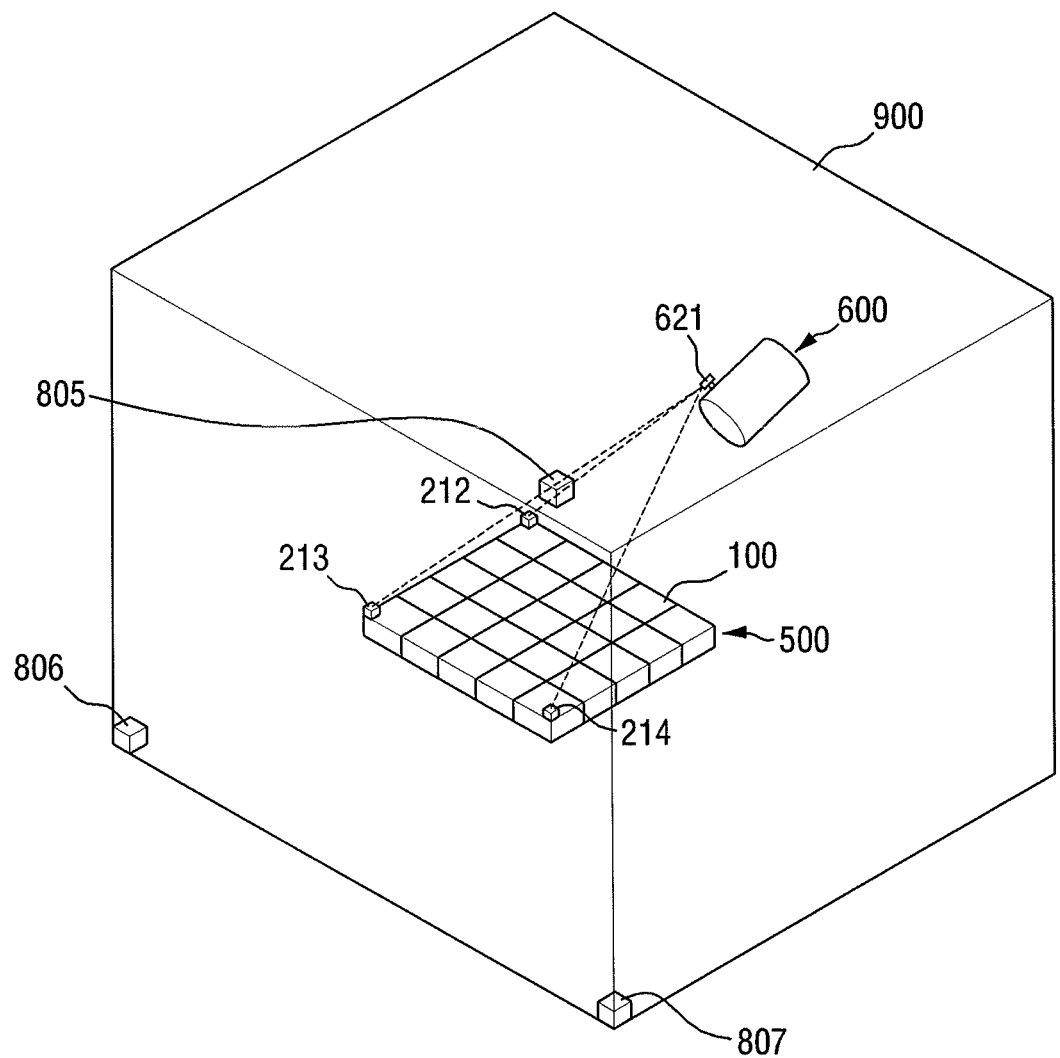
FIG. 7 is a schematic diagram showing an X-ray detection system according to a further embodiment.

FIG. 7 is a schematic diagram showing an X-ray detection system according to a further embodiment. Referring to FIG. 7, the present embodiment is different from that of FIG. 3 in that an external sensor unit is further included.

The external sensor unit may include, for example, a fifth wireless transceiver 805, a sixth wireless transceiver 806, and a seventh wireless transceiver 807. The fifth to seventh wireless transceivers 805, 806, and 807 may be installed outside an X-ray detector 500. In an exemplary embodiment, the fifth to seventh wireless transceivers 805, 806, and 807 may be installed in an X-ray imaging room 900 or an X-ray imaging chamber in which the X-ray generation device 600 and the X-ray detector 500 are arranged. When the X-ray imaging room 900 or chamber has the shape of a rectangular parallelepiped, the fifth to seventh wireless transceivers 805, 806, and 807 may be installed at the third corners of the bottom surface of the X-ray imaging room 900 or chamber.

The fifth to seventh wireless transceivers 805, 806, and 807 may define a 3D coordinate system. For example, it can be understood that the fifth wireless transceiver 805 is arranged at the origin of the 3D coordinate system, the sixth wireless transceiver 806 is arranged on an X axis of the 3D coordinate system, and the seventh wireless transceiver 807 is arranged on a Y axis of the 3D coordinate system.

The fifth to seventh wireless transceivers 805, 806, and 807 can calculate the distances between them and the first wireless transceiver 621 by communicating with the first wireless transceiver 621. For example, a time synchronization signal is input to the first wireless transceiver 621 and the fifth to seventh wireless transceivers 805, 806, and 807. Then, the respective times are synchronized among the first wireless transceiver 621 and the fifth to seventh wireless transceivers 805, 806, and 807. Thereafter, the first wireless transceiver 621 transmits a wireless signal, and compares the times at which the fifth to seventh wireless transceivers 805, 806, and 807 receive the wireless signal with one another, so that distances between the transceivers can be calculated.

Accordingly, the relative location of the first wireless transceiver 621 to the bottom surface of the X-ray imaging room 900 or chamber can be determined, and the location coordinates of the first wireless transceiver 621 in the 3D coordinate system can be determined.

Similar to this, each of the second to fourth wireless transceivers 212, 213, and 214 can calculate distances between the corresponding wireless transceiver and the fifth to seventh wireless transceivers 805, 806, and 807 by communicating with the fifth to seventh wireless transceivers 805, 806, and 807. Accordingly, the relative locations of the second to fourth wireless transceiver 212, 213, and 214 to the bottom surface of the X-ray imaging room 900 or chamber can be determined, and the location coordinates thereof in the 3D coordinate system can be determined.

The distances between the first wireless transceiver 621 and the second to fourth wireless transceivers 212, 213, and 214 and straight lines for individually connecting the first wireless transceiver 621 and the second to fourth wireless transceivers 212, 213, and 214 can be calculated using the location coordinates of the first wireless transceiver 621 and the location coordinates of the second to fourth wireless transceivers 212, 213, and 214. Thereafter, as described above with reference to the embodiment of FIG. 1, correction data can be computed, and digital data signals corrected in consideration of the correction data can be generated.

In accordance with the present embodiment, the relative locations of the X-ray generation device 600 and the X-ray detector 500 can be more exactly calculated, thus enabling more precise correction data to be computed.

For more precise calculation, the X-ray generation device 600 may further include a first gyro sensor 622, and the X-ray detector 500 may further include a second gyro sensor 215.

By way of summation and review, according to one or more embodiments, even if the center line of X-rays emitted from an X-ray generation device is inclined without being perpendicular to an X-ray detector, the X-ray detector corrects the amount of X-rays incident on pixels using distance data obtained from a first wireless transceiver and second to fourth wireless transceivers, thus preventing degradation of image quality.

In contrast, in typical movable X-ray detection systems, an angle at which emitted X-rays are incident on an X-ray detector is not fixed. When the incident angle is not a right angle, the amount of X-rays incident on each pixel of an X-ray detection unit varies, so that the quality of a finally output image may be degraded.

Although the exemplary embodiments have been disclosed for illustrative purposes, those skilled in the art will appreciate that various modifications, additions and substitutions are possible, without departing from the scope and spirit of the invention as disclosed in the accompanying claims. Therefore, it should be noted that the above-described embodiments are not restrictive, but are exemplary from all aspects.

What is claimed is:

1. An X-ray detection system, comprising:
    an X-ray generation device including an X-ray emission unit and a first sensor unit including a first sensor; and
    an X-ray detector including:
        an X-ray reception unit for receiving X-rays from the X-ray emission unit;
        a data detection unit for detecting data from the X-ray reception unit;
        a second sensor unit, the second sensor unit including a second sensor, a third sensor, and a fourth sensor, wherein
        the first and second sensor units compute a first distance between the first sensor and the second sensor, a second distance between the first sensor and the third sensor, and a third distance between the first sensor unit and the fourth sensor;
        a computation unit for receiving the first, second, and third distances from the first and second sensor units, and for computing correction data using mutual differences of the first, second, and third distances, the correction data for correcting an amount of X-ray incident on the X-ray detector; and
        a data correction unit for receiving a data signal from the data detection unit, receiving the correction data from the computation unit, and then calibrating the data signal by applying the correction data to the data signal.

2. The X-ray detection system of claim 1, wherein:
the first to fourth sensors are wireless transceivers, respectively, and
the second sensor, third sensor, and fourth sensor individually communicate with the first sensor.

3. The X-ray detection system of claim 2, wherein:
the X-ray detector has a shape of a first quadrangle including a first corner, a second corner, a third corner, and a fourth corner, and
the second, third, and fourth wireless transceivers are arranged at the second, third, and fourth corners, respectively.

4. The X-ray detection system of claim 3, wherein the correction data includes a ratio of areas obtained by dividing an area of a second quadrangle by an area of the first quadrangle, wherein the second quadrangle is defined by points respectively present on a first straight line for connecting the first sensor and the first corner, a second straight line for connecting the first sensor and the second corner, a third straight line for connecting the first sensor and the third corner, and a fourth straight line for connecting the first sensor and the fourth corner, and the points are individually located at an identical distance from the first sensor.

5. The X-ray detection system of claim 1, further comprising an external sensor unit installed outside the X-ray generation device and the X-ray detector.

6. The X-ray detection system of claim 5, wherein:
the external sensor unit includes a fifth sensor, a sixth sensor, and a seventh sensor,
the X-ray generation device and the X-ray detector are arranged in an X-ray imaging room, and
the fifth to seventh sensors are arranged at corners of a bottom surface of the X-ray imaging room.

7. The X-ray detection system of claim 1, wherein a center line of the X-rays incident on the X-ray reception unit from the X-ray emission unit forms an acute angle or an obtuse angle with respect to the X-ray reception unit.

8. The X-ray detection system of claim 1, wherein each of the X-ray generation device and the X-ray detector is movable.

9. The X-ray detection system of claim 1, wherein:
the first sensor unit further includes a first gyro sensor and the second sensor unit includes a second gyro sensor.

10. The X-ray detection system of claim 1, wherein:
the correction data is for calibrating difference between an amount of X-ray emitted from the X-ray emission unit and an amount of X-ray incident on the X-ray detector, and
the difference between the amounts of X-ray emitted from the X-ray emission unit and X-ray incident on the X-ray detector is caused by mutual differences of the first, second, and third distances.

11. An X-ray detection system, comprising:
an X-ray generation device including an X-ray emission unit and a first wireless transceiver; and
an X-ray detector including a first corner, a second corner, a third corner, and a fourth corner, the X-ray detector including:
an X-ray reception unit for receiving X-rays from the X-ray emission unit, and
a second wireless transceiver, a third wireless transceiver, and a fourth wireless transceiver arranged at the first, second, and third corners, respectively, wherein:
the X-ray detector calculates:
an area of a first quadrangle defined by the first, second, third, and fourth corners;
an area of a second quadrangle defined by a first point on a first line for connecting the X-ray generation device and the first corner, a second point on a second line for connecting the X-ray generation device and the second corner, a third point on a third line for connecting the X-ray generation device and the third corner, and a fourth point on a fourth line for connecting the X-ray generation device and the fourth corner, the first, second, third, and fourth points being located at an identical distance from the X-ray generation device; and
a ratio of the areas of the first and second quadrangles by dividing the area of the second quadrangle by the area of the first quadrangle, wherein
the X-ray detector corrects an amount of X-rays incident on the X-ray detector from the X-ray generation device using the ratio of the areas of the first and second quadrangle.

12. The X-ray detection system of claim 11, further comprising a fifth wireless transceiver, a sixth wireless transceiver, and a seventh wireless transceiver arranged at corners of a bottom surface of an X-ray imaging room,
wherein the X-ray generation device and the X-ray detector are arranged in the X-ray imaging room.

13. The X-ray detection system of claim 11, wherein the X-ray detector further comprises a gyro sensor.

14. The X-ray detector of claim 13, further comprising a gyro sensor arranged at a center portion of the X-ray reception unit.

15. An X-ray detection method, comprising:
defining a first corner, a second corner, a third corner, and a fourth corner of a first quadrangle in an X-ray detector;
obtaining a first straight line for connecting an X-ray generation device and the first corner, a second straight line for connecting the X-ray generation device and the second corner, a third straight line for connecting the X-ray generation device and the third corner, and a fourth straight line for connecting the X-ray generation device and the fourth corner;
calculating an area of a second quadrangle defined by points present on the respective straight lines, the points being individually located at an identical distance from the X-ray generation device;
calculating a ratio of areas by dividing the area of the second quadrangle by an area of the first quadrangle; and
correcting an amount of X-rays incident on the X-ray detector from the X-ray generation device using the ratio of areas.

16. The X-ray detection method of claim 15, wherein correcting the amount of incident X-rays comprises dividing the amount of X-rays incident on the X-ray detector by the ratio of areas.

17. The X-ray detection method of claim 15, wherein the identical distance is a minimum value of distances from the X-ray generation device to the first to fourth corners.

* * * * *